(12) United States Patent
Nakaoka et al.

(10) Patent No.: US 8,808,266 B2
(45) Date of Patent: Aug. 19, 2014

(54) PANTS-TYPE DISPOSABLE DIAPER

(75) Inventors: Kenji Nakaoka, Osaka (JP); Yuki Takahashi, Tsurugi-cho (JP)

(73) Assignee: Livedo Corporation, Shikokuchuo-shi (JP)

( * ) Notice: Subject to any disclaimer, the term of this patent is extended or adjusted under 35 U.S.C. 154(b) by 264 days.

(21) Appl. No.: 13/376,681

(22) PCT Filed: Jul. 13, 2010

(86) PCT No.: PCT/JP2010/004535
§ 371 (c)(1),
(2), (4) Date: Dec. 7, 2011

(87) PCT Pub. No.: WO2011/018876
PCT Pub. Date: Feb. 17, 2011

(65) Prior Publication Data
US 2012/0095430 A1    Apr. 19, 2012

(30) Foreign Application Priority Data

Aug. 13, 2009  (JP) .................. 2009-187778

(51) Int. Cl.
*A61F 13/496* (2006.01)
*A61F 13/49* (2006.01)
*A61F 13/495* (2006.01)

(52) U.S. Cl.
CPC ......... *A61F 13/496* (2013.01); *A61F 13/49019* (2013.01); *A61F 13/495* (2013.01); *A61F 13/49017* (2013.01)
USPC .................................................. 604/385.25

(58) Field of Classification Search
USPC ....................... 604/385.24, 385.25
See application file for complete search history.

(56) References Cited

U.S. PATENT DOCUMENTS 5,836,931 A    11/1998  Toyoda et al.
7,226,438 B2 *  6/2007  Soga et al. ............... 604/385.25
(Continued)

FOREIGN PATENT DOCUMENTS

DE    10 2007 002290 A1    7/2008
EP       1 997 464 A1    12/2008
(Continued)

OTHER PUBLICATIONS

Japanese Office Action dated Jun. 4, 2013, issued in corresponding Japanese Patent Application No. 2009-187778, with English translation (5 pages).

(Continued)

*Primary Examiner* — Susan Su
(74) *Attorney, Agent, or Firm* — Westerman, Hattori, Daniels & Adrian, LLP (57) ABSTRACT

A pants-type disposable diaper 1 comprising: a diaper main body 2 having a front part P, a back part Q, and a crotch part R therebetween, and having a waist opening 3 and a pair of leg openings 4; an absorbent core 10 disposed at the crotch part R; a first elastic member 13 disposed continuously, and having a first crotch-crossing part 13A which extends across the crotch part R and a first leg opening edge part 13B which extends along edges 15 of a front side of the both leg openings 4; and a second elastic member 14 disposed so as to be spaced from the first elastic member 13, and having a second crotch-crossing part 14A which extends intermittently across the crotch part R and a second leg opening edge part 14B which extends along edges 15 of a back side of the both leg openings 4.

8 Claims, 4 Drawing Sheets

(56) References Cited

U.S. PATENT DOCUMENTS

| | | | |
|---|---|---|---|
| 7,530,972 B2* | 5/2009 | Ando et al. | 604/385.27 |
| 7,777,094 B2* | 8/2010 | Mori et al. | 604/367 |
| 2002/0007172 A1* | 1/2002 | Takei et al. | 604/385.27 |
| 2002/0049421 A1* | 4/2002 | Hayase et al. | 604/385.27 |
| 2002/0068919 A1* | 6/2002 | Shinohara et al. | 604/385.27 |
| 2002/0072728 A1* | 6/2002 | Shinohara et al. | 604/385.29 |
| 2003/0000620 A1* | 1/2003 | Herrin et al. | 156/62.2 |
| 2003/0078556 A1* | 4/2003 | Sasaki et al. | 604/385.25 |
| 2003/0083638 A1* | 5/2003 | Molee | 604/385.27 |
| 2003/0196253 A1* | 10/2003 | Rajala et al. | 2/401 |
| 2004/0035521 A1* | 2/2004 | Nakakado et al. | 156/229 |
| 2006/0064069 A1* | 3/2006 | Rajala et al. | 604/385.24 |
| 2006/0174400 A1* | 8/2006 | Kurata | 2/400 |
| 2008/0027406 A1* | 1/2008 | Shirai et al. | 604/385.24 |
| 2008/0065036 A1* | 3/2008 | Minato et al. | 604/367 |
| 2008/0071241 A1* | 3/2008 | Bittner et al. | 604/385.27 |
| 2008/0300565 A1* | 12/2008 | Takahashi et al. | 604/367 |
| 2008/0300568 A1 | 12/2008 | Fujioka et al. | |
| 2009/0005751 A1* | 1/2009 | Shirai et al. | 604/385.29 |
| 2009/0177176 A1* | 7/2009 | Saito | 604/385.29 |
| 2009/0275911 A1 | 11/2009 | Hormung et al. | |
| 2009/0299319 A1* | 12/2009 | Takahashi et al. | 604/385.25 |
| 2010/0076394 A1* | 3/2010 | Hayase et al. | 604/385.29 |
| 2010/0094239 A1* | 4/2010 | Nakaoka et al. | 604/385.25 |
| 2010/0286646 A1* | 11/2010 | Takino et al. | 604/385.3 |
| 2010/0318053 A1* | 12/2010 | Smet | 604/385.23 |

FOREIGN PATENT DOCUMENTS

| | | |
|---|---|---|
| EP | 2 133 053 A1 | 12/2009 |
| JP | 6-296643 A | 10/1994 |
| JP | 2002-172132 A | 6/2002 |
| JP | 2006-149749 A | 6/2006 |
| JP | 2007-097646 A | 4/2007 |

OTHER PUBLICATIONS

International Search Report of PCT/JP2010/004535, mailing date Oct. 26, 2010.

Japanese Office Action dated Feb. 4, 2014, issued in Japanese Patent Application No. 2009-187778, w/English translation, (6 pages).

* cited by examiner

PANTS-TYPE DISPOSABLE DIAPER

TECHNICAL FIELD

The present invention relates to a pants-type disposable diaper for an infant or an adult.

BACKGROUND ART

Conventionally, there is known a pants-type disposable diaper. For example, Japanese Laid-Open Patent Publication No. 6-296643 (Patent Literature 1) discloses a pants-type disposable diaper comprising a first elastic member disposed continuously so as to extend across a crotch part and along edges of a front side of both leg openings, and a second elastic member disposed continuously so as to extend across the crotch part and along edges of a back side of the both leg openings.

CITATION LIST

Patent Literature

Patent Literature 1
Japanese Laid-Open Patent Publication No. 6-296643

SUMMARY OF INVENTION

Technical Problem

When wearing a conventional pants-type disposable diaper, a male wearer may feel discomfort or tightness around the genitalia. Further, when a large amount of urine is excreted at one time, the urine cannot be sufficiently absorbed by an absorbent core, and may laterally leak from the diaper.

The present invention has been achieved in view of the above circumstances, and an object of the present invention is to provide a pants-type disposable diaper which is excellent in feel of wearing for a male wearer and can absorb urine into an absorbent core certainly even when a large amount of urine is excreted at one time.

Solution to Problem

The pants-type disposable diaper of the present invention which solves the above problems comprises: a diaper main body having a front part, a back part, and a crotch part positioned between the front part and the back part, and having a waist opening and a pair of leg openings formed by joining the front part and the back part; an absorbent core disposed at the crotch part; a first elastic member disposed continuously to the diaper main body, and having a first crotch-crossing part which extends across the crotch part and a first leg opening edge part which extends along edges of a front side of the both leg openings; and a second elastic member disposed to the diaper main body so as to be spaced from the first elastic member, and having a second crotch-crossing part which extends intermittently across the crotch part and a second leg opening edge part which extends along edges of a back side of the both leg openings.

In the pants-type disposable diaper of the present invention, a pocket is formed on a front side of the diaper by the first elastic member, and the pocket can receive a male genitalia, and therefore, feel of wearing of the diaper is improved for a male wearer. In addition, even when a large amount of urine is excreted at one time, the urine can be temporarily stored in the pocket, and then, the absorbent core is permitted to absorb the urine slowly. Therefore, lateral leakage of the urine is less likely to occur.

A center between the first crotch-crossing part and the second crotch-crossing part is preferably located anterior to a center of the diaper main body in a front-back direction. According to this structure, the first crotch-crossing part of the first elastic member comes to be disposed on a front side of the center of the diaper main body in the front-back direction. Therefore, a male genitalia is tend to be received suitably in the pocket formed by the first elastic member, and urine is easily stored temporarily in the pocket due to an appropriate positional relation with an urethra. In order that these effects may be exerted more certainly, a backmost part of the first crotch-crossing part is preferably located at a region of 30 mm or more and 90 mm or less from the center of the diaper main body in the front-back direction.

The second elastic member is preferably spaced from the first elastic member at a distance of 10 mm or more and 50 mm or less. According to this structure, leg gathers are formed along the edges of the both leg openings appropriately, thereby preventing leakage of excrement such as urine and the like from the crotch part. Further, stretching and contracting of the first elastic member are less likely to be impaired by the second elastic member, and therefore, the suitable pocket is easily formed by the first elastic member.

Advantageous Effects of Invention

The pants-type disposable diaper of the present invention is excellent in feel of wearing for a male wearer, and can absorb urine into the absorbent core certainly even when a large amount of urine is excreted at one time.

DESCRIPTION OF EMBODIMENTS

A pants-type disposable diaper of the present invention comprises a diaper main body having a front part, a back part, and a crotch part positioned between the front part and the back part. In the diaper main body, a waist opening and a pair of leg openings are formed by joining the front part and the back part. In detail, the front part and the back part are joined at their both side edges in a width direction of the diaper, thereby forming the pair of leg openings on both sides of the crotch part and the waist opening provided by edges, with respect to a front-back direction of the diaper, of the front part and the back part.

Concerning names of respective parts of the diaper main body, a part applied to an abdomen side of a wearer is called the front part, a part applied to a buttocks side of the wearer is called the back part, and a part positioned between the front part and the back part and applied to a crotch of the wearer is called the crotch part, in a state of wearing the pants-type disposable diaper. The crotch part is a middle part when the pants-type disposable diaper is divided into three parts in the front-back direction in a state where the front part and the back part of the diaper are disjoined and the diaper is developed on a plane, and the crotch part is a part whose side edges in the width direction are not joined when the diaper is formed in a shape of pants. Thus, the leg openings are formed on only both sides of the crotch part.

The front-back direction means a direction from the front part toward the back part and vice versa of the pants-type disposable diaper. The term "front" means a direction from the back part toward the front part, and the term "back" means a direction from the front part toward the back part. The width direction means a direction orthogonal to the front-back direction on the same plane as the pants-type disposable diaper in a state where the pants-type disposable diaper is developed on a plane.

The pants-type disposable diaper of the present invention has an absorbent core disposed at the crotch part. The absorbent core is disposed at least at the crotch part, and further, may also extend to the front part and/or the back part.

In one embodiment of the diaper main body provided with the absorbent core, for example, a laminate comprising a liquid-permeable top sheet, a liquid-impermeable back sheet, and the absorbent core interposed therebetween may have the front part, the back part and the crotch part therebetween. In another embodiment of the diaper main body provided with the absorbent core, the diaper main body having the front part, the back part and the crotch part therebetween may be formed from a laminate comprising an inner sheet and an outer sheet; and an absorbent body in which the absorbent core is interposed between a liquid-permeable top sheet and a liquid-impermeable back sheet may be provided on an inner surface, that faces a wearer in wearing, of the inner sheet.

The top sheet is preferably made of a liquid-permeable material, and the back sheet is preferably made of a liquid-impermeable or water-repellent material. The inner sheet is preferably made of a hydrophilic or water-repellent material, and the outer sheet is preferably made of a water-repellent material.

The absorbent core is not particularly limited as long as it absorbs excrement such as urine and the like, and it preferably contains an absorbent resin. The absorbent core can be obtained, for example, by the steps of mixing a granular absorbent resin with a hydrophilic fiber assembly such as crushed pulp fibers, cellulose fibers and the like to obtain a clump, or dispersing the granular absorbent resin to the hydrophilic fiber assembly to obtain a clump; wrapping the clump with a paper sheet such as a tissue paper and the like, or with a cover sheet such as a liquid-permeable nonwoven fabric sheet and the like; and molding the obtained wrapped clump into a predefined shape such as a rectangular shape, an hourglass shape, a center nipped-in gourd shape, a battledore shape, and the like.

Rising flaps are preferably provided along edges of opposite sides, with respect to the width direction, of the absorbent core. For example, the rising flaps may be provided on an upper surface of the absorbent core at both sides in the width direction, or may be provided outside the absorbent core in the width direction. In the embodiment that the absorbent core is interposed between the top sheet and the back sheet, the rising flaps are joined, for example, to the top sheet, the back sheet folded back to an upper surface of the top sheet, or both the top sheet and the back sheet. The rising flaps are preferably made of a liquid-impermeable plastic film, a water-repellent nonwoven fabric, or the like, and more preferably made of a water-repellent nonwoven fabric. The rising flaps enable to prevent lateral leakage of urine and the like.

A rising elastic member is preferably disposed at an upper end (an end nearer to a wearer) of the rising flap in a state of rising. The rising flap forms a rising gather which rises toward a wearer due to a contraction force of the rising elastic member, thereby preventing lateral leakage of urine and the like. An inner surface of the rising flap may be joined to the top sheet at ends, with respect to the front-back direction of the diaper, of the rising flaps, thereby preventing leakage of urine and the like in the front-back direction.

The pants-type disposable diaper of the present invention comprises a first elastic member disposed so as to extend across the crotch part and along edges of a front side of the both leg openings, and a second elastic member disposed so as to extend across the crotch part and along edges of a back side of the both leg openings. Thus, the first elastic member has a first crotch-crossing part which extends across the crotch part and a first leg opening edge part which extends along the edges of the front side of the both leg openings; and the second elastic member has a second crotch-crossing part which extends across the crotch part and a second leg opening edge part which extends along the edges of the back side of the both leg openings. Each of the first and second leg opening edge parts has two portions, that is, one portion disposed along the edges of the right leg openings of the pants-type disposable diaper and the other portion disposed along the edges of the left leg openings of the pants-type disposable diaper. Both ends of the crotch-crossing part connect the each leg opening edge part.

The first and second elastic members are disposed at least at the crotch part, and further, may also extend to the front part and/or the back part. Preferably, the first and second elastic members extend to a part where the front part and the back part are joined.

The second elastic member is provided so as to be spaced from the first elastic member wholly. Thus, the first elastic member and the second elastic member neither contact nor intersect each other.

The first and second leg opening edge parts are respectively disposed continuously. The first leg opening edge part and the second leg opening edge part cooperate with each other to form leg gathers around a leg of a wearer, resulting in preventing leakage of excrement such as urine and the like from the crotch part. The first and second leg opening edge parts mean parts where the first and second elastic member are disposed along the edges of the leg openings. The first and second leg opening edge parts are not necessarily disposed at the absolute edges of the leg openings, but are generally located at 5 mm or more inward from the edges of the leg openings.

Concerning the crotch-crossing part, the second crotch-crossing part is disposed intermittently, whereas the first crotch-crossing part is disposed continuously. Thus, the first elastic member is disposed continuously so as to extend across the crotch part and along edges of the front side of the both leg openings.

Due to the first elastic member which is disposed continuously so as to extend across the crotch part and along edges of the front side of the both leg openings, a pocket which extends from the first crotch-crossing part to the first leg opening edge part is formed on the front side of the diaper. In the pants-type disposable diaper of the present invention, since the first elastic member is disposed so as to be spaced from the second elastic member, and the second elastic member is disposed so as to extend intermittently across the crotch part, stretching and contracting of the first elastic member are less likely to be impaired by the second elastic member, and hence, the suitable pocket is easily formed by the first elastic member.

Concerning the pocket, if the second elastic member is also disposed continuously throughout, for example, the first crotch-crossing part of the first elastic member is pulled toward the second elastic member, and the deep pocket is unlikely to be formed. However, in the pants-type disposable diaper of the present invention, since the second crotch-crossing part of the second elastic member is disposed intermittently across the crotch part, the deeper pocket is easily formed by the first elastic member.

The pocket formed by the first elastic member is convenient particularly for receiving a male genitalia. When a male wearer stands or lies, the genitalia can be received in the pocket without the wearer feeling tightness, and hence, feel of wearing of the diaper is improved. In addition, even when a large amount of urine is excreted at one time, the urine can be temporarily stored in the pocket, and then, the absorbent core is permitted to absorb the urine slowly. Therefore, lateral leakage of the urine is less likely to occur.

Further, in the pants-type disposable diaper of the present invention, since the second elastic member is disposed so as to extend intermittently across the crotch part, the contraction force of the second crotch-crossing part of the second elastic member is reduced, whereby pressing against the wearer becomes weak. As a result, the entirety of the buttocks is less likely to be pressed by the elastic member, and therefore, stools are likely to be received suitably. In addition, the appearance of the diaper around the buttocks becomes simple and improved when the diaper is worn.

The first elastic member and the second elastic member are preferably disposed so as to be entirely displaced toward the front side from a center of the diaper in the front-back direction. Thus, in the pants-type disposable diaper of the present invention, a center between the first crotch-crossing part and the second crotch-crossing part is preferably located anterior to a center of the diaper main body in the front-back direction. According to this structure, the first crotch-crossing part of the first elastic member is disposed on the front side relative to the center of the diaper main body in the front-back direction. Therefore, a male genitalia is tend to be received suitably in the pocket formed by the first elastic member, and urine is easily stored temporarily in the pocket due to an appropriate positional relation with an urethra. In addition, the second crotch-crossing part of the second elastic member is likely to be located around a bottom of the diaper, thereby improving the appearance of the diaper around the buttocks in wearing the diaper.

The center between the first crotch-crossing part and the second crotch-crossing part means a center, with respect to the front-back direction of the diaper, of a region between the first crotch-crossing part and the second crotch-crossing part, and is assumed as a line extending substantially in the width direction of the diaper. In this case, the first and second crotch-crossing parts mean parts extending across the crotch part and located at 30 mm or more inward from the edges of the leg openings. The center of the diaper main body in the front-back direction means a center line between the edges of the waist opening on the front and back parts in a state where the front part and the back part of the pants-type disposable diaper are disjoined from each other and the diaper main body is developed on a plane, and is normally located at the bottom of the diaper. The center between the first crotch-crossing part and the second crotch-crossing part, and the center of the diaper main body in the front-back direction, are determined in a state where the diaper is fully spread, namely, in a state where the elastic member of the diaper is fully stretched.

Preferably, the first elastic member is disposed so that the first crotch-crossing part is located anterior to the center of the diaper main body in the front-back direction. Specifically, a backmost part of the first crotch-crossing part is preferably located at a region of 30 mm or more and 90 mm or less (more preferably at a region of 40 mm or more and 80 mm or less) from the center of the diaper main body in the front-back direction. When the backmost part of the first crotch-crossing part is located anterior to the center of the diaper main body at a region of 30 mm or more and 90 mm or less from the center of the diaper main body in the front-back direction, a male genitalia is received suitably in the pocket formed by the first elastic member, and urine is easy to be stored temporarily in the pocket.

Preferably, the second elastic member is spaced from the first elastic member at a distance of 10 mm or more and 50 mm or less (more preferably at a distance of 20 mm or more and 40 mm or less). When the second elastic member is spaced from the first elastic member at the distance of 50 mm or less, the leg gathers are formed appropriately along the edges of the both leg openings, resulting in preventing leakage of excrement such as urine and the like from the crotch part certainly. When the second elastic member is spaced from the first elastic member at the distance of 10 mm or more, stretching and contracting of the first elastic member are less likely to be impaired by the second elastic member, thereby forming the pocket by the first elastic member appropriately. In addition, it becomes easy to provide the second crotch-crossing part intermittently while providing the first crotch-crossing part continuously.

The distance by which the second elastic member is spaced from the first elastic member means a minimum value of a distance between the first elastic member and the second elastic member in the front-back direction of the diaper. Preferably, the distance coincide with a distance between a backmost part of the first elastic member and a frontmost part of the second elastic member.

The first crotch-crossing part preferably includes the backmost part of the first elastic member. In this case, the first elastic member is provided in a shape that is convex toward the bottom of the diaper. As a result, a male genitalia is received suitably in the pocket formed by the first elastic member, and urine is easy to be stored temporarily in the pocket. The second crotch-crossing part preferably includes the frontmost part of the second elastic member.

The first and second elastic members may consist of one or a plurality of elastic members; and preferably consist of 2 to 5 of elastic members, respectively. In the case that the first and second elastic members consist of a plurality of elastic members, even if one elastic member is broken, the remaining elastic member(s) can maintain stretch and elastic properties. In addition, by disposing a plurality of elastic members side by side, wearing feel can be made soft while maintaining a high stretching force.

The first and second elastic members are preferably disposed to the diaper main body in a stretched state. Specifically, the first elastic member is preferably disposed to the diaper main body in a stretched state from one portion of the first leg opening edge part through the first crotch-crossing part to the other portion of the first leg opening edge part, and fixed to the diaper main body by means of an adhesive or the like. The second elastic member is preferably disposed to the diaper main body in a stretched state from one portion of the second leg opening edge part through the second crotch-crossing part to the other portion of the second leg opening edge part, and the second crotch-crossing part is preferably cut after at least the second leg opening edge part is fixed to the diaper main body by means of an adhesive or the like. Here, in light of manufacturing efficiency, it is preferred that the second crotch-crossing part is also fixed to the diaper main body by means of an adhesive or the like and then cut at multiple locations. The cutting of the second crotch-crossing part may be performed, for example, by holding the diaper main body, in which the elastic member is disposed, between a flat roll and a roll cutter having multiple cutting blades on its surface, and then forwarding it.

The first and second elastic members are preferably provided between two sheets. For example, when the diaper main body is composed of a laminate comprising a liquid-permeable top sheet, a liquid-impermeable back sheet, and an absorbent core interposed therebetween, respective elastic members are preferably disposed between the top sheet and the back sheet. When the diaper main body is composed of a laminate comprising an inner sheet and an outer sheet; and an absorbent body in which an absorbent core is interposed between a top sheet and a back sheet is provided on the surface of the inner sheet on a wearer side, the respective elastic members are preferably provided between the inner sheet and the outer sheet.

The pants-type disposable diaper of the present invention may further comprise a waist elastic member disposed along the edge of the waist opening, and a body elastic member disposed in the front part and the back part so as to extend in the width direction of the diaper, in addition to the first and second elastic members. The waist elastic member prevents excrement such as urine and the like from leaking from a back side or an abdomen side, even when a wearer lies. The body elastic member improves a fitting property of the diaper around an abdomen region. The waist elastic member and the body elastic member are preferably provided between two sheets, similarly to the first and second elastic members.

Elastic materials such as a polyurethane thread, a polyurethane film, a natural rubber and the like, which are generally used for disposable diapers, can be used for the respective elastic members. The respective elastic members are preferably fixed in a stretched state with a hot-melt adhesive. For example, a polyurethane thread having a fineness of 100 dtex to 2,500 dtex is stretched at a ratio of 1.1 to 5.0 times to be fixed. A preferable hot-melt adhesive is a rubber hot-melt adhesive.

Next, an example of the pants-type disposable diaper of the present invention is explained, referring to drawings. However, the present invention is not restricted to the following embodiment.

Figure 1:
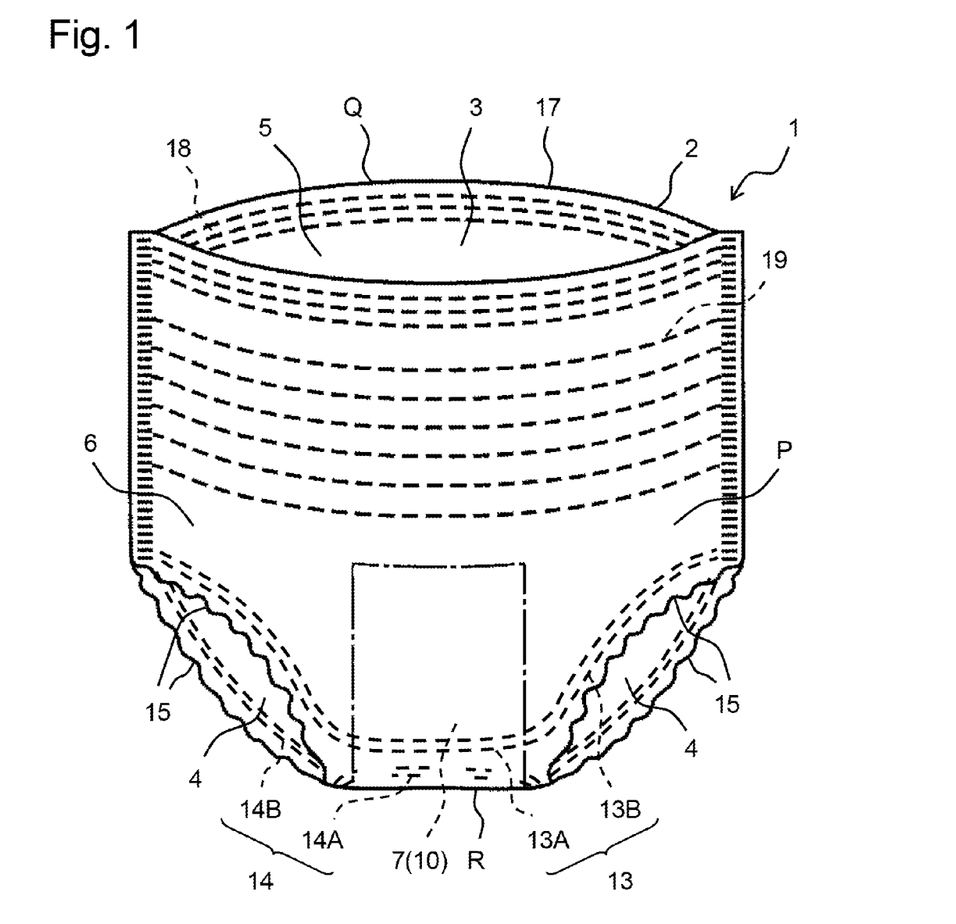
FIG. 1 shows a perspective view of a pants-type disposable diaper of the present invention.
Figure 2:
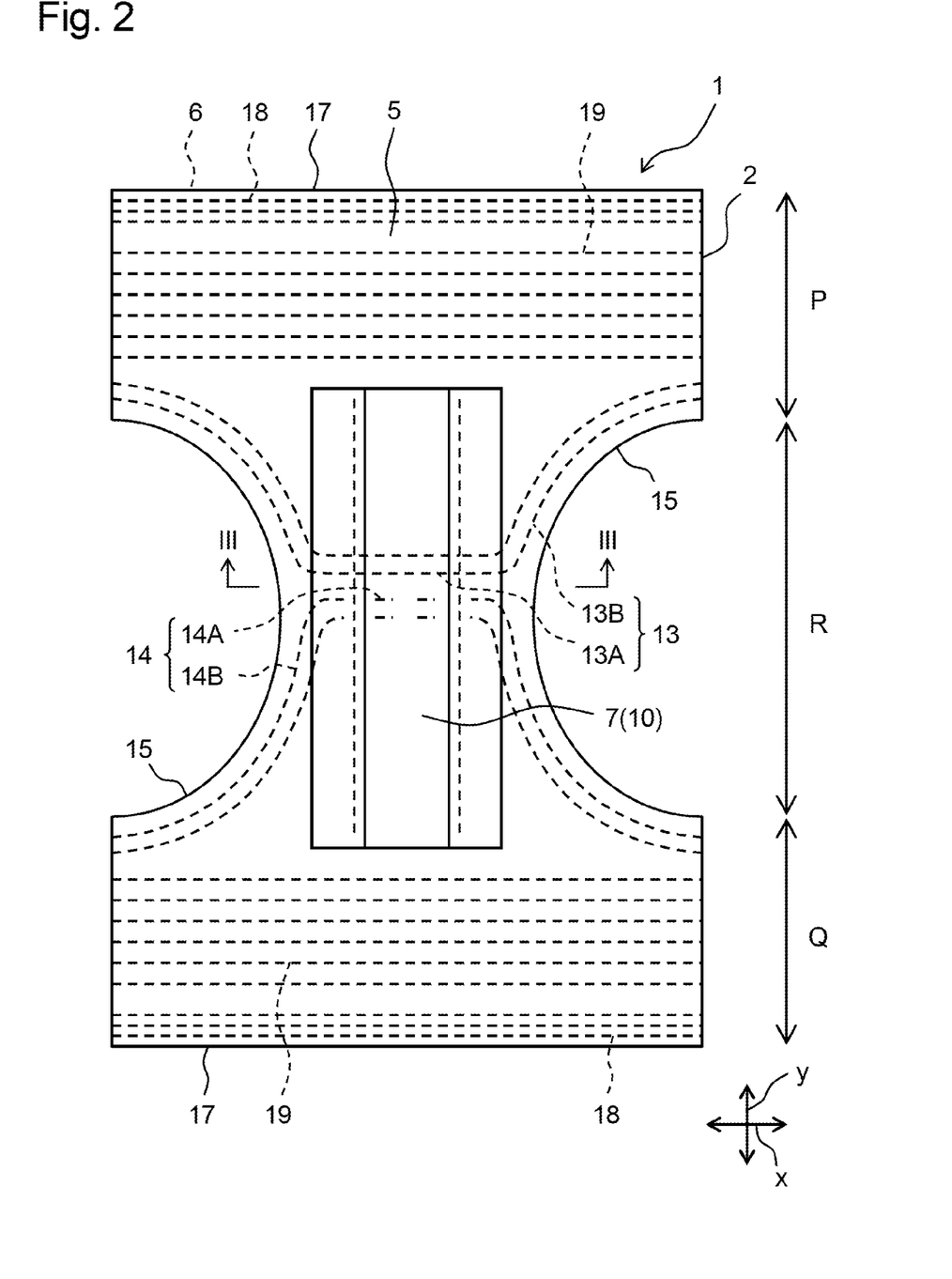
FIG. 2 shows a plan view of the pants-type disposable diaper shown in FIG. 1 in a developed state in which a front part and a back part are disjoined.
Figure 3:
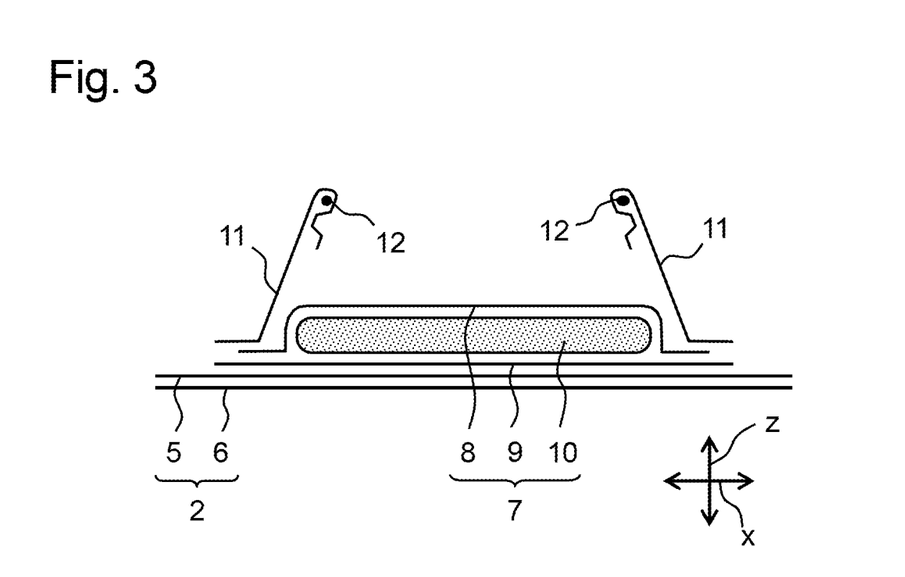
FIG. 3 shows a cross-sectional view taken along line in FIG. 2.
Figure 4:
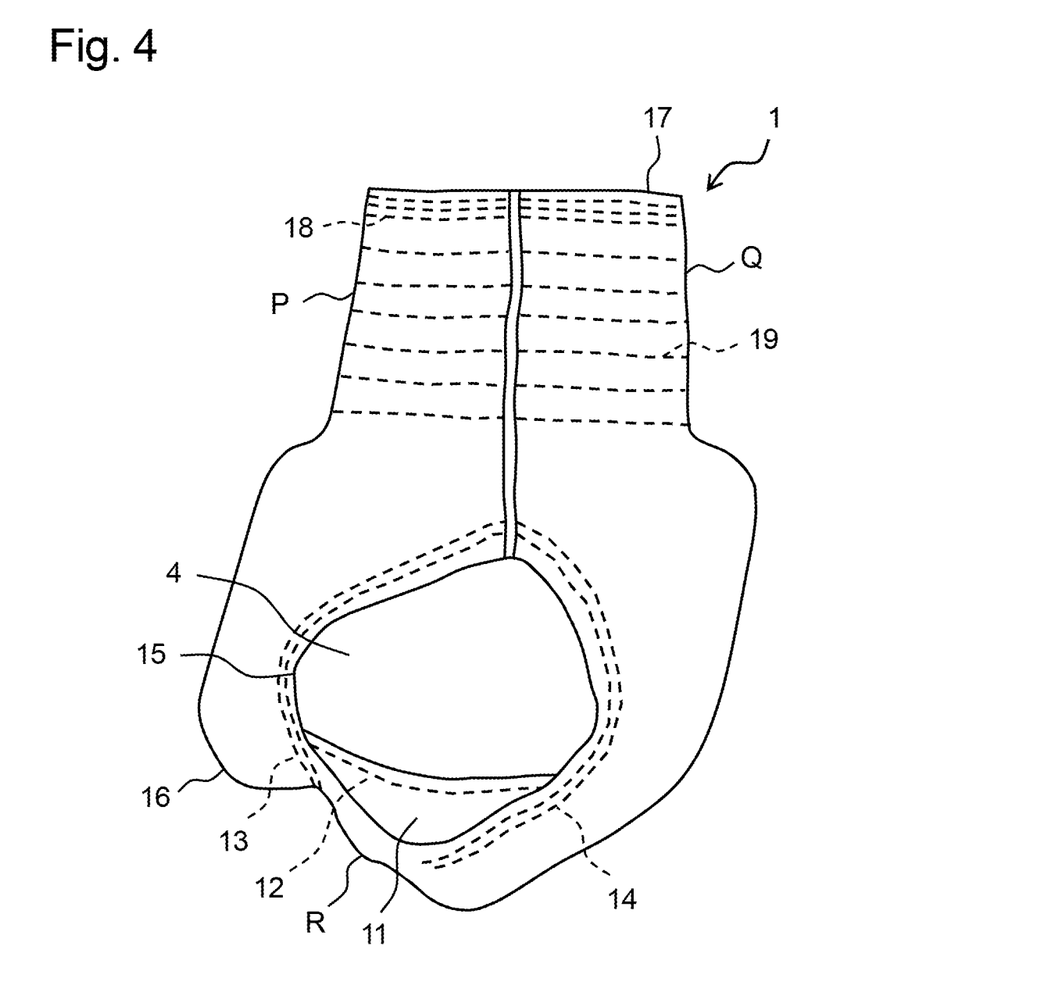
FIG. 4 shows a lateral view of the pants-type disposable diaper shown in FIG. 1.

FIG. 1 shows a perspective view of a pants-type disposable diaper of the present invention. FIG. 2 shows a plan view of the pants-type disposable diaper shown in FIG. 1 in a developed state in which a front part and a back part are disjoined. FIG. 3 shows a cross-sectional view taken along line III-III in FIG. 2. FIG. 4 shows a lateral view of the pants-type disposable diaper shown in FIG. 1. In the drawings, the arrow x direction represents a width direction of the diaper, and the arrow y represents a front-back direction of the diaper. The direction perpendicular to the plane formed by the arrows x and y is defined as a thickness direction z.

A pants-type disposable diaper 1 comprises a diaper main body 2 having a front part P, a back part Q, and a crotch part R positioned between the front part P and the back part Q, and having a waist opening 3 and a pair of leg openings 4 formed by joining the front part P and the back part Q. The diaper main body 2 is composed of a laminate comprising an inner sheet 5 and an outer sheet 6.

The pants-type disposable diaper 1 comprises an absorbent core 10 disposed at the crotch part R. In detail, the pants-type disposable diaper 1 comprises an absorbent body 7 disposed on an inner surface of the diaper main body 2 at the crotch part R and comprising a top sheet 8, a back sheet 9, and an absorbent core 10 interposed between the top sheet 9 and the back sheet 10, as shown in FIG. 3. The top sheet 8 is placed so as to face a wearer's skin at a crotch, and allows excrement such as urine and the like to permeate through. The excrement that permeated the top sheet 8 is accommodated in the absorbent core 10. The back sheet 9 is attached to the inner sheet 5 of the diaper main body 2, and prevents the excrement from permeating outside.

Rising flaps 11 are provided along edges of opposite sides, with respect to the width direction x, of the absorbent core 10 (FIG. 3). The rising flap 11, which extends in the front-back direction y of the diaper, is joined astride the top sheet 8 and the back sheet 9. A rising elastic member 12 is disposed at an inner end in the width direction x of the rising flap 11. A rising gather which rises upward (toward a wearer) is formed from the rising flap 11 due to a contraction force of the rising elastic member 12, thereby preventing lateral leakage of urine and the like. An inner surface of the rising flaps 11 is joined to the top sheet 8 at front and back ends of the absorbent body 7, thereby preventing leakage of urine and the like outward in the front-back direction y.

A first elastic member 13 is disposed to the diaper main body 2 so as to extend across the crotch part R and along edges 15 of a front side of the both leg openings 4. The first elastic member 13 has a first crotch-crossing part 13A which extends across the crotch part R and a first leg opening edge part 13B which extends along the edges 15 of the front side of the both leg openings 4. In the first elastic member 13, both of the first crotch-crossing part 13A and the first leg opening edge part 13B are disposed continuously and provided between the inner sheet 5 and the outer sheet 6. Here, though the first elastic member 13 is disposed continuously, it is shown as a dashed line in the drawing because it is not recognized directly in appearance.

A second elastic member 14 is disposed to the diaper main body 2 so as to be spaced from the first elastic member 13 and extend across the crotch part R and along edges 15 of a back side of the both leg openings 4. The second elastic member 14 has a second crotch-crossing part 14A which extends across the crotch part R and a second leg opening edge part 14B which extends along the edges 15 of the back side of the both leg openings 4. In the second elastic member 14, the second crotch-crossing part 14A is disposed intermittently, whereas the second leg opening edge part 14B is disposed continuously. The second elastic member 14 is provided between the inner sheet 5 and the outer sheet 6. Because the second elastic member 14 is not recognized directly in appearance, even a part which is disposed continuously is shown as a dashed line.

The first elastic member 13 and the second elastic member 14 are disposed so that a center between the first crotch-crossing part 13A of the first elastic member 13 and the second crotch-crossing part 14A of the second elastic member 14 is located anterior to a center of the diaper main body 2 in the front-back direction y.

In the pants-type disposable diaper 1, the first leg opening edge part 13B of the first elastic member 13 and the second leg opening edge part 14B of the second elastic member 14 cooperate with each other to form leg gathers along the edges 15 of the both leg openings 4, thereby preventing leakage of excrement such as urine and the like from the crotch part R. In addition, a pocket 16 is formed on the front side of the pants-type disposable diaper 1 by the first elastic member 13, as shown in FIG. 4. The pocket 16 is suitable for receiving a male genitalia, and urine can be temporarily stored in the pocket 16.

In the diaper main body 2, a waist elastic member 18 is disposed along an edge 17 of the waist opening 3, and a body elastic member 19 is disposed in the front part P and the back part Q so as to extend in the width direction x of the diaper. The waist elastic member 18 and the body elastic member 19 are also provided between the inner sheet 5 and the outer sheet 6.

REFERENCE SIGNS LIST

1: a pants-type disposable diaper
2: a diaper main body
10: an absorbent core
13: a first elastic member
14: a second elastic member
16: a pocket

The invention claimed is:

1. A pants-type disposable diaper comprising:
a diaper main body having a front part, a back part, and a crotch part positioned between the front part and the back part, and having a waist opening and a pair of leg openings formed by joining the front part and the back part;
an absorbent core disposed at the crotch part;
a first elastic member disposed continuously to the diaper main body, and having a first crotch-crossing part which extends across the crotch part and a first leg opening edge part which extends along edges of a front side of both leg openings; and
a second elastic member disposed to the diaper main body so as to be spaced from the first elastic member, and having a second crotch-crossing part which extends intermittently across the crotch part and a second leg opening edge part which extends along edges of a back side of both leg openings.

2. The pants-type disposable diaper according to claim 1, wherein a center between the first crotch-crossing part and the second crotch-crossing part is located anterior to a center of the diaper main body in a front-back direction.

3. The pants-type disposable diaper according to claim 2, wherein a backmost part of the first crotch-crossing part is located at a region of 30 mm or more and 90 mm or less from the center of the diaper main body in the front-back direction.

4. The pants-type disposable diaper according to claim 1, wherein the second elastic member is spaced from the first elastic member at a distance of 10 mm or more and 50 mm or less.

5. The pants-type disposable diaper according to claim 2, wherein the second elastic member is spaced from the first elastic member at a distance of 10 mm or more and 50 mm or less.

6. The pants-type disposable diaper according to claim 3, wherein the second elastic member is spaced from the first elastic member at a distance of 10 mm or more and 50 mm or less.

7. The pants-type disposable diaper according to claim 1, wherein both ends of the second crotch-crossing part connect to the second leg opening edge part.

8. The pants-type disposable diaper according to claim 1, wherein the first leg opening edge part and the second leg opening edge part cooperate with each other to form leg gathers around the leg openings.

\* \* \* \* \*